US011375908B2

(12) United States Patent
Jiang et al.

(10) Patent No.: US 11,375,908 B2
(45) Date of Patent: Jul. 5, 2022

(54) BLOOD PRESSURE DETECTION SIGNAL SAMPLING AND COMPENSATION METHOD AND APPARATUS, AND BLOOD PRESSURE SIGNAL COLLECTION SYSTEM

(71) Applicant: HUAWEI TECHNOLOGIES CO., LTD., Guangdong (CN)

(72) Inventors: Yongtao Jiang, Shenzhen (CN); Yu Zhu, Shenzhen (CN); Peida Xu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 1016 days.

(21) Appl. No.: 16/072,265

(22) PCT Filed: Oct. 21, 2016

(86) PCT No.: PCT/CN2016/102823
§ 371 (c)(1),
(2) Date: Jul. 24, 2018

(87) PCT Pub. No.: WO2018/072195
PCT Pub. Date: Apr. 26, 2018

(65) Prior Publication Data
US 2019/0046053 A1   Feb. 14, 2019

(51) Int. Cl.
*A61B 5/021*  (2006.01)
*A61B 5/00*  (2006.01)
(Continued)

(52) U.S. Cl.
CPC .......... *A61B 5/02125* (2013.01); *A61B 5/318* (2021.01); *A61B 5/7225* (2013.01);
(Continued)

(58) Field of Classification Search
CPC ... A61B 5/318; A61B 5/02125; A61B 5/7278; A61B 5/7225; A61B 5/0245;
(Continued)

(56) References Cited

U.S. PATENT DOCUMENTS 4,676,253 A    6/1987  Newman et al.
10,039,463 B1 * 8/2018  Selvaraj ................. A61B 5/316
(Continued)

FOREIGN PATENT DOCUMENTS

CN    1493002 A    4/2004
CN    1582845 A    2/2005
(Continued)

OTHER PUBLICATIONS

Feifei Yang,"Research and Implementation of Wireless Synchronization Acquisition System for Multi-channel Physiological Signals",Northeastern Universitydated Dec. 31, 2015,total 72 pages.
(Continued)

*Primary Examiner* — An H Do
(74) *Attorney, Agent, or Firm* — Fish & Richardson P.C.

(57) ABSTRACT

Blood pressure detection signal sampling and compensation methods and apparatuses, and an example blood pressure signal collection system are described. One example method described includes controlling an electrocardiogram (ECG) sampling module and a photoplethysmogram (PPG) sampling module to simultaneously sample a standard periodic signal. Sampling frequencies and sampling end times are separately obtained. A sampling start time and a sampling frequency of the ECG sampling module or the PPG module is then compensated so that a sampling frequency deviation is less than a preset frequency threshold and a sampling end time difference is less than a preset time threshold.

18 Claims, 4 Drawing Sheets

(51) Int. Cl.
*G16H 50/20* (2018.01)
*G16H 40/63* (2018.01)
*G06F 1/12* (2006.01)
*H03M 1/12* (2006.01)
*A61B 5/318* (2021.01)
*A61B 5/0245* (2006.01)
*A61B 5/024* (2006.01)

(52) U.S. Cl.
CPC .............. *A61B 5/7278* (2013.01); *G06F 1/12* (2013.01); *G16H 40/63* (2018.01); *G16H 50/20* (2018.01); *H03M 1/1255* (2013.01); *A61B 5/0245* (2013.01); *A61B 5/02416* (2013.01)

(58) Field of Classification Search
CPC .... A61B 5/02416; G16H 50/20; G16H 40/63; G06F 1/12; H03M 1/1255
See application file for complete search history.

(56) References Cited

U.S. PATENT DOCUMENTS

| | | | |
|---|---|---|---|
| 10,485,433 B2 * | 11/2019 | Baxi | A61B 5/6802 |
| 10,758,143 B2 * | 9/2020 | Gui | A61B 5/7221 |
| 2005/0261593 A1 | 11/2005 | Zhang et al. | |
| 2011/0066044 A1 | 3/2011 | Moon et al. | |
| 2011/0196244 A1 | 8/2011 | Ribas Ripoll et al. | |
| 2015/0313486 A1 | 11/2015 | Mestha et al. | |
| 2015/0366469 A1 | 12/2015 | Harris et al. | |
| 2015/0366473 A1 | 12/2015 | Shimuta et al. | |

FOREIGN PATENT DOCUMENTS

| | | |
|---|---|---|
| CN | 1698536 A | 11/2005 |
| CN | 201142678 Y | 10/2008 |
| CN | 100471035 C | 3/2009 |
| CN | 101484068 A | 7/2009 |
| CN | 100586366 C | 2/2010 |
| CN | 101947111 A | 1/2011 |
| CN | 101958726 A | 1/2011 |
| CN | 102058400 A | 5/2011 |
| CN | 102186411 A | 9/2011 |
| CN | 102478422 A | 5/2012 |
| CN | 102857196 A | 1/2013 |
| CN | 103248593 A | 8/2013 |
| CN | 103516654 A | 1/2014 |
| CN | 104095655 A | 10/2014 |
| CN | 104257371 A | 1/2015 |
| CN | 104856661 A | 8/2015 |
| CN | 105007809 A | 10/2015 |
| CN | 106028272 A | 10/2016 |

OTHER PUBLICATIONS

International Search Report issued in International Application No. PCT/CN2016/102823 dated Jul. 12, 2017, 15 pages.
Yubo et al.,"Integrated Testing Technology and Application of Intelligent Substation",dated Dec. 2013, 4 pages (With English Abstract).
Xia et al., "Proceedings of the research on the development of modem small satellite technology in China-A real-time integration adjustment method based on time synchronization",dated 2015, 6 pages (With English Abstract).
China News Agency,"2010 China Radio and TV Yearbook",dated 2010, 5 pages (With English Abstract).
Hongzan,"CNC machining process (second edition)", dated 2004, 7 pages (With English Abstract).
Office Action issued in Chinese Application No. 201680029853.5 dated May 18, 2020, 40 pages (With English Translation).
Office Action issued in Chinese Application No. 201680029853.5 dated Sep. 24, 2019, 38 pages (with English translation).

* cited by examiner

BLOOD PRESSURE DETECTION SIGNAL SAMPLING AND COMPENSATION METHOD AND APPARATUS, AND BLOOD PRESSURE SIGNAL COLLECTION SYSTEM

CROSS-REFERENCE TO RELATED APPLICATIONS

This application is a national stage of International Application No. PCT/CN2016/102823, filed on Oct. 21, 2016, which is hereby incorporated by reference in its entirety.

TECHNICAL FIELD

Embodiments of the present invention relate to the field of blood pressure detection technologies, and in particular, to a blood pressure detection signal sampling and compensation method and apparatus, and a blood pressure signal collection system.

BACKGROUND

A blood pressure (Blood Pressure, BP) is a lateral pressure, that is, pressure intensity, acting on a vascular wall per unit area when blood flows inside a blood vessel. The blood pressure is an important physiological index that reflects a human cardiovascular function, and is of great significance in a disease diagnosis, quality effect observation, a prognosis, and the like.

In recent years, with the rapid development of intelligent terminals, wearable devices, and mobile medical technologies, convenience of blood pressure monitoring has been gradually improved, so that people pay more attention to family blood pressure monitoring and dynamic blood pressure monitoring.

Many studies show that there is a positive correlation between a velocity at which a pulse propagates along an artery a pulse wave velocity (Pulse Wave Velocity, PWV) and an arterial blood pressure. A common PWV measurement method is calculating a pulse wave transit time (Pulse Transit Time, PTT), that is, a time required for a pulse wave to move from the heart to a point on the artery. By using the PTT to measure the blood pressure, a measured person does not need to use a cuff, and no damage is caused to tissues or blood vessels under a measurement apparatus. This can provide a convenient and comfortable blood pressure measurement manner for a user. In addition, a structure may be small and light, and is suitable for application of a portable or wearable product.

Basically, the PTT measurement method is synchronously collecting an electrocardiogram (electrocardiogram, ECG) signal and a photoplethysmogram (Photoplethysmography, PPG) signal, and identifying an R wave of the ECG signal and a maximum point of the PPG signal, so as to obtain a delay time PTT. A mathematical model relationship is established between the PTT and the blood pressure, so as to finally obtain values of a systolic blood pressure and a diastolic blood pressure. Because the ECG signal and the PPG signal are sampled separately, there may be a deviation in sampling time and frequency precision. A sampling deviation directly affects precision of subsequent blood pressure mathematical modeling. Consequently, precision of blood pressure measurement using the PWV method is affected.

SUMMARY

Embodiments of the present invention provide a blood pressure detection signal sampling and compensation method and apparatus, and a blood pressure signal collection system, so as to improve precision of a blood pressure detection signal.

According to a first aspect, a blood pressure detection signal sampling and compensation method is provided, including:

controlling an ECG sampling module and a PPG module to simultaneously sample a standard periodic signal;

separately obtaining sampling frequencies and sampling end times of the ECG sampling module and the PPG sampling module for the standard periodic signal;

compensating for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold;

compensating for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold; and compensating for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold.

According to the blood pressure detection signal sampling and compensation method provided in the present invention, the ECG sampling module and the PPG sampling module are controlled to sample an ECG signal and a PPG signal of a to-be-detected user and sample the standard periodic signal, so as to obtain a sampling end time difference between the ECG signal and the PPG signal, and the sampling frequency deviations of the ECG sampling module and the PPG sampling module for the standard periodic signal, thereby compensating for the sampling start time of the ECG sampling module or the PPG sampling module and compensating for the sampling frequencies of the ECG sampling module and the PPG sampling module. In this way, the sampling end time difference between the ECG signal and the PPG signal is less than the preset time threshold, and the sampling frequency deviations of the ECG sampling module and the PPG sampling module for the standard periodic signal are less than the preset frequency threshold, so that an error of a PTT determined by using the ECG sampling module and the PPG sampling module falls within an allowed range, and an error of a blood pressure value measured by using a PTT method falls within an allowed range, thereby improving precision of blood pressure measurement performed by using the PTT method.

In a possible implementation of the first aspect, before the controlling an ECG sampling module and a PPG sampling module to simultaneously sample a standard periodic signal, the method further includes:

generating a high-precision clock signal, where precision of the high-precision clock signal is one order of magnitude higher than precision of clock signals in the ECG sampling module and the PPG sampling module;

the controlling an ECG sampling module and a PPG sampling module to simultaneously sample a standard periodic signal includes:

controlling, based on the high-precision clock signal, the ECG sampling module and the PPG sampling module to simultaneously sample the standard periodic signal; and the separately obtaining sampling frequencies and sampling end times of the ECG sampling module and the PPG sampling module for the standard periodic signal includes:

recording the sampling end times of the ECG sampling module and the PPG sampling module for the standard periodic signal based on the high-precision clock signal.

The high-precision clock signal can ensure precise recording of the sampling start times and the sampling end times of the ECG sampling module and the PPG sampling module, and ensure a stable frequency of the standard periodic signal generated based on the high-precision clock signal.

In a possible implementation of the first aspect, the high-precision clock signal is generated by any one of a high-precision system crystal oscillator, a synchronization calibration clock signal of a Bluetooth module, and a synchronization calibration clock signal of a WiFi module; and the high-precision clock signal includes:

any one of a sine wave signal, a triangular wave signal, and a sawtooth signal.

In a possible implementation of the first aspect, before the controlling an ECG sampling module and a PPG sampling module to separately sample a standard periodic signal, the method further includes:

generating the standard periodic signal based on the high-precision clock signal.

In a possible implementation of the first aspect, the controlling an ECG sampling module and a PPG sampling module to separately sample a standard periodic signal includes:

controlling the ECG sampling module to sample the standard periodic signal, and calculating a frequency $f_1$ of sampled data; and controlling the PPG sampling module to sample the standard periodic signal, and calculating a frequency $f_2$ of sampled data;

the separately obtaining sampling frequencies and sampling end times of the ECG sampling module and the PPG sampling module for the standard periodic signal includes:

calculating $\Delta f_{10}=|f_1-f_0|$ and $\Delta f_{20}=|f_2-f_0|$, where $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal;

the compensating for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold includes:

if $\Delta f_{10}>F_0$ and $f_1>f_0$, reducing data sampled by the ECG sampling module by a quantity L, where $(\Delta f_{10}-F_0)\le L\le \Delta f_{10}$, and using $(F_1-L)$ as a new sampling frequency of the ECG sampling module, where $F_1$ is an original sampling frequency of the ECG sampling module, and $F_0$ is the preset frequency threshold; or if $\Delta f_{10}>F_0$ and $f_1<f_0$, increasing data sampled by the ECG sampling module by a quantity M, where $(\Delta f_{10}-F_0)\le M\le \Delta f_{10}$, and using $(F_1+M)$ as a new sampling frequency of the ECG sampling module; and the compensating for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold includes:

if $\Delta f_{20}>F_0$ and $f_2>f_0$, reducing data sampled by the PPG sampling) module by a quantity N, where $(\Delta f_{20}-F_0)\le N\le \Delta f_{20}$, and using $(F_2-N)$ as a new sampling frequency of the PPG sampling module, where $F_2$ is an original sampling frequency of the PPG sampling module; or if $\Delta f_{20}>F_0$ and $f_2<f_0$, increasing data sampled by the PPG sampling) module by a quantity P, where $(\Delta f_{20}-F_0)\le P\le \Delta f_{20}$, and using $(F_2+P)$ as a new sampling frequency of the PPG sampling module.

In a possible implementation of the first aspect, the compensating for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold includes:

calculating the sampling end time difference $\Delta t_{21}$ between the ECG sampling module and the PPG sampling module for the standard periodic signal, where $\Delta t_{21}=|t_2-t_1|$, $t_1$ is a sampling end time of the ECG sampling module for the standard periodic signal, and $t_2$ is a sampling end time of the PPG sampling module for the standard periodic signal; and delaying a sampling time-to-trigger $t_{p1}$ of the ECG sampling module if $\Delta t_{21}>T_0$ and $t_2>t_1$, so that $T_0<|t_{p1}-t_{p2}|<\Delta t_{21}$ is met, where $t_{p2}$ is a sampling time-to-trigger of the PPG sampling module, and $T_0$ is the preset time threshold; or delaying a sampling time-to-trigger $t_{p2}$ of the PPG sampling module if $\Delta t_{21}>T_0$ and $t_2>t_1$, so that $T_0<|t_{p1}-t_{p2}|<\Delta t_{21}$ is met.

According to a second aspect, a blood pressure detection signal sampling and compensation apparatus is provided, including:

a control module, configured to control an ECG sampling module and a PPG module to simultaneously sample a standard periodic signal;

a calculation module, configured to separately obtain sampling frequencies and sampling end times of the ECG sampling module and the PPG sampling module for the standard periodic signal; and a compensation module, configured to: compensate for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold; compensate for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold; and compensate for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold.

In a possible implementation of the second aspect, the blood pressure detection signal sampling and compensation apparatus further includes: a clock module, configured to generate a high-precision clock signal, where precision of the high-precision clock signal is one order of magnitude higher than precision of clock signals in the ECG sampling module and the PPG sampling module; and the control module is specifically configured to: control, based on the high-precision clock signal, the ECG sampling module and the PPG sampling module to simultaneously sample the standard periodic signal, and record the sampling end times of the ECG sampling module and the PPG sampling module for the standard periodic signal based on the high-precision clock signal.

In a possible implementation of the second aspect, the high-precision clock signal is generated by any one of a high-precision system crystal oscillator, a synchronization calibration clock signal of a Bluetooth module, and a synchronization calibration clock signal of a WiFi module; and the high-precision clock signal includes:

any one of a sine wave signal, a triangular wave signal, and a sawtooth signal.

In a possible implementation of the second aspect, the calculation module is further configured to generate the standard periodic signal based on the high-precision clock signal.

In a possible implementation of the second aspect, the control module is specifically configured to: control the ECG sampling module to sample the standard periodic signal, and calculate a frequency $f_1$ of sampled data; and control the PPG sampling module to sample the standard periodic signal, and calculate a frequency $f_2$ of sampled data;

the calculation module is specifically configured to calculate $\Delta f_{10}=|f_1-f_0|$ and $\Delta f_{20}=|f_2-f_0|$, where $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal; and the compensation module is specifically configured to: if $\Delta f_{10}>F_0$ and $f_1>f_0$, reduce data sampled by the ECG sampling module by a quantity L, where $(\Delta f_{10}-F_0) \leq L \leq \Delta f_{10}$, and use $(F_1-L)$ as a new sampling frequency of the ECG sampling module, where $F_1$ is an original sampling frequency of the ECG sampling module, and $F_0$ is the preset frequency threshold; if $\Delta f_{10}>F_0$ and $f_1<f_0$, increase data sampled by the ECG sampling module by a quantity M, where $(\Delta f_{10}-F_0) \leq M \leq \Delta f_{10}$, and use $(F_1+M)$ as a new sampling frequency of the ECG sampling module; if $\Delta f_{20}>F_0$ and $f_2>f_0$, reduce data sampled by the PPG sampling module by a quantity N, where $(\Delta f_{20}-F_0) \leq N \leq \Delta f_{20}$, and use $(F_2-N)$ as a new sampling frequency of the PPG sampling module, where $F_2$ is an original sampling frequency of the PPG sampling module; or if $\Delta f_{20}>F_0$ and $f_2<f_0$, increase data sampled by the PPG sampling module by a quantity P, where $(\Delta f_{20}-F_0) \leq P \leq \Delta f_{20}$, and use $(F_2+P)$ as a new sampling frequency of the PPG sampling module.

In a possible implementation of the second aspect, the calculation module is further configured to calculate the sampling end time difference $\Delta t_{21}$ between the sampling module and the PPG sampling module for the standard periodic signal, where $\Delta t_{21}=|t_2-t_1|$, $t_1$ is a sampling end time of the ECG sampling module for the standard periodic signal, and $t_2$ is a sampling end time of the PPG sampling module for the standard periodic signal; and the compensation module is specifically configured to delay a sampling time-to-trigger $t_{p1}$ of the ECG sampling module if $\Delta t_{21}>T_0$ and $t_2>t_1$, so that $T_0<|t_{p1}-t_{p2}|<\Delta t_{21}$ is met, where $t_{p2}$ is a sampling time-to-trigger of the PPG sampling module, and $T_0$ is the preset time threshold; or delay a sampling time-to-trigger $t_{p2}$ of the PPG sampling module if $\Delta t_{21}>T_0$ and $t_2<t_1$, so that $T_0<|t_{p1}-t_{p2}|<\Delta t_{21}$ is met.

According to a third aspect, a blood pressure signal sampling system is provided, including an ECG sampling module, a PPG sampling module, and a processor, where the processor is configured to: control the ECG sampling module and the PPG module to simultaneously sample a standard periodic signal; separately obtain sampling frequencies and sampling end times of the ECG sampling module and the PPG sampling module for the standard periodic signal; compensate for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold; compensate for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold; and compensate for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold.

In a possible implementation of the third aspect, the blood pressure signal sampling system further includes: a clock module, configured to generate a high-precision clock signal, where precision of the high-precision clock signal is one order of magnitude higher than precision of clock signals in the ECG sampling module and the PPG sampling module; and the processor is specifically configured to: control, based on the high-precision clock signal, the ECG sampling module and the PPG sampling module to simultaneously sample the standard periodic signal, and record the sampling end times of the ECG sampling module and the PPG sampling module for the standard periodic signal based on the high-precision clock signal.

In a possible implementation of the third aspect, the clock module includes any one of a high-precision system crystal oscillator, a clock module in a Bluetooth module, and a clock module in a WiFi module;

the high-precision clock signal is generated by any one of the high-precision system crystal oscillator, a synchronization calibration clock signal of the Bluetooth module, and a synchronization calibration clock signal of the WiFi module; and the high-precision clock signal includes:

any one of a sine wave signal, a triangular wave signal, and a sawtooth signal.

In a possible implementation of the third aspect, the processor is further configured to generate the standard periodic signal based on the high-precision clock signal.

In a possible implementation of the third aspect, the processor is specifically configured to: control the ECG sampling module to sample the standard periodic signal, and calculate a frequency $f_1$ of sampled data; control the PPG sampling module to sample the standard periodic signal, and calculate a frequency $f_2$ of sampled data; calculate $\Delta f_{10}=|f_1-f_0|$ and $\Delta f_{20}=|f_2-f_0|$, where $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal; and if $\Delta f_{10}>F_0$ and $f_1>f_0$, reduce data sampled by the ECG sampling module by a quantity L, where $(\Delta f_{10}-F_0) \leq L \leq \Delta f_{10}$, and use $(F_1-L)$ as a new sampling frequency of the ECG sampling module, where $F_1$ is an original sampling frequency of the ECG sampling module, and $F_0$ is the preset frequency threshold; if $\Delta f_{10}>F_0$ and $f_1<f_0$, increase data sampled by the ECG sampling module by a quantity M, where $(\Delta f_{10}-F_0) \leq M \leq \Delta f_{10}$, and use $(F_1+M)$ as a new sampling frequency of the ECG sampling module; if $\Delta f_{20}>F_0$ and $f_2>f_0$, reduce data sampled by the PPG sampling module by a quantity N, where $(\Delta f_{20}-F_0) \leq N \leq \Delta f_{20}$, and use $(F_2-N)$ as a new sampling frequency of the PPG sampling module, where $F_2$ is an original sampling frequency of the PPG sampling module; or if $\Delta f_{20}>F_0$ and $f_2<f_0$, increase data sampled by the PPG sampling module by a quantity P, where $(\Delta f_{20}-F_0) \leq P \leq \Delta f_{20}$, and use $(F_2+P)$ as a new sampling frequency of the PPG sampling module.

In a possible implementation of the third aspect, the processor is specifically configured to: calculate the sampling end time difference $\Delta t_{21}$ between the ECG sampling module and the PPG sampling module for the standard periodic signal, where $\Delta t_{21}=|t_2-t_1|$, $t_1$ is a sampling end time of the ECG sampling module for the standard periodic signal, and $t_2$ is a sampling end time of the PPG sampling module for the standard periodic signal; and delay a sampling time-to-trigger $t_{p1}$ of the ECG sampling module if $\Delta t_{21}>T_0$ and $t_2>t_1$, so that $T_0<|t_{p1}-t_{p2}|<\Delta t_{21}$ is met, where $t_{p2}$ is a sampling time-to-trigger of the PPG sampling module, and $T_0$ is the preset time threshold; or delay a sampling time-to-trigger $t_{p2}$ of the PPG sampling module if $\Delta t_{21}>T_0$ and $t_2<t_1$, so that $T_0<|t_{p1}-t_{p2}|<\Delta t_{21}$ is met.

According to the blood pressure detection signal sampling and compensation method and apparatus, and the blood pressure signal collection system that are provided in the embodiments of the present invention, the ECG sampling module and the PPG sampling module are controlled to sample the ECG signal and the PPG signal of the to-be-detected user and sample the standard periodic signal, so as to obtain the sampling end time difference between the ECG signal and the PPG signal, and the sampling frequency deviations of the ECG sampling module and the PPG sampling module for the standard periodic signal, thereby compensating for the sampling start time of the ECG sampling module or the PPG sampling module and compensating for the sampling frequencies of the ECG sampling module and the PPG sampling module. In this way, the sampling end time difference between the ECG signal and the PPG signal is less than the preset time threshold, and the sampling frequency deviations of the ECG sampling module and the PPG sampling module for the standard periodic signal are less than the preset frequency threshold, so that the error of the PTT determined by using the ECG sampling module and the PPG sampling module falls within the allowed range, and the error of the blood pressure value measured by using the PTT method falls within the allowed range, thereby improving the precision of blood pressure measurement performed by using the PTT method.

BRIEF DESCRIPTION OF DRAWINGS

To describe the technical solutions in the embodiments of the present invention or in the prior art more clearly, the following briefly describes the accompanying drawings required for describing the embodiments or the prior art. Apparently, the accompanying drawings in the following description show some embodiments of the present invention, and persons of ordinary skill in the art may still derive other drawings from these accompanying drawings without creative efforts.

DESCRIPTION OF EMBODIMENTS

To make the objectives, technical solutions, and advantages of the embodiments of the present invention clearer, the following clearly and completely describes the technical solutions in the embodiments of the present invention with reference to the accompanying drawings in the embodiments of the present invention. Apparently, the described embodiments are some but not all of the embodiments of the present invention. All other embodiments obtained by persons of ordinary skill in the art based on the embodiments of the present invention without creative efforts shall fall within the protection scope of the present invention.

When a PTT method is used to measure a blood pressure, an ECG signal and a PPG signal of a user need to be measured synchronously, a PTT is obtained by analyzing the ECG signal and the PPG signal, and then values of a systolic blood pressure and a diastolic blood pressure are obtained by using a relationship between the PTT and the blood pressure. The ECG signal and the PPG signal are respectively sampled by using a corresponding ECG sampling module and PPG sampling module. However, because sampling frequencies and sampling times of the ECG sampling module and the PPG sampling module may have deviations, the PTT obtained by analyzing the ECG signal and the PPG signal may have a deviation. Consequently, a finally obtained blood pressure value may be affected.

Therefore, the embodiments of the present invention provide a blood pressure detection signal sampling and compensation method, so as to compensate for signals collected by the ECG sampling module and the PPG sampling module, so that a deviation of the finally measured blood pressure value is less than a preset threshold.

Figure 1:
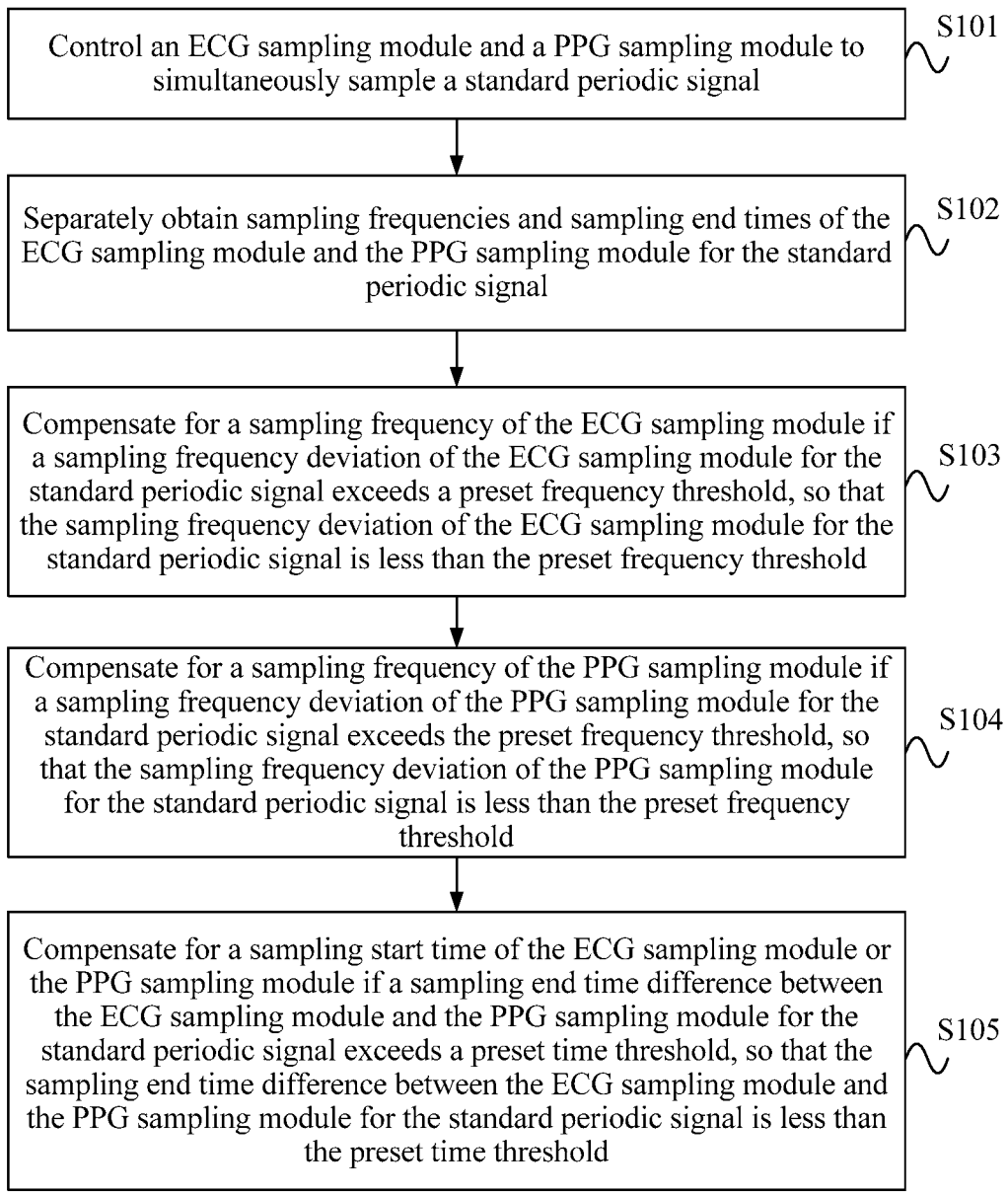
FIG. 1 is a flowchart of Embodiment 1 of a blood pressure detection signal sampling and compensation method according to an embodiment of the present invention.

FIG. 1 is a flowchart of Embodiment 1 of a blood pressure detection signal sampling and compensation method according to an embodiment of the present invention. As shown in FIG. 1, the method provided in this embodiment includes the following steps.

Step S101: Control an ECG sampling module and a PPG sampling module to simultaneously sample a standard periodic signal.

Specifically, an ECG signal and a PPG signal are respectively collected by the ECG sampling module and the PPG sampling module, and the ECG sampling module and the PPG sampling module are mutually independent. Therefore, sampling times and sampling frequencies of the ECG sampling module and the PPG sampling module may have deviations. Consequently, there is a deviation in time synchronization or frequency synchronization of the ECG signal and the PPG signal that are obtained through sampling. As a result, there is an error in a PTT. Therefore, to resolve the PTT error, a sampling time deviation between and sampling frequency deviations of the ECG sampling module and the PPG sampling module need to be eliminated. In this case, the sampling time deviation between and the sampling frequency deviations of the ECG sampling module and the PPG sampling module need to be measured first, so that the sampling times and the sampling frequencies of the ECG sampling module and the PPG sampling module can be compensated for. In this way, the PTT error is reduced to an allowed range, so that an error of a blood pressure value measured by using a PTT method falls within an allowed range.

To measure the sampling time deviation between and the sampling frequency deviations of the ECG sampling module and the PPG sampling module, the ECG sampling module and the PPG sampling module may be separately controlled to simultaneously sample a standard periodic signal.

Step S102: Separately obtain sampling frequencies and sampling end times of the ECG sampling module and the PPG sampling module for the standard periodic signal.

First, when the ECG sampling module and the PPG sampling module are separately controlled to sample the standard periodic signal, sampling frequencies of signals obtained through sampling by the ECG sampling module and the PPG sampling module are separately recorded, and the sampling end times are separately recorded.

A timer may be used to control the ECG sampling module and the PPG sampling module to simultaneously perform sampling. A controller simultaneously sends a sampling notification message to the ECG sampling module and the PPG sampling module based on triggering of the timer, so that the ECG sampling module and the PPG sampling module simultaneously perform measurement. Because the PTT needs to be obtained by performing synchronous comparison on the signals collected by the ECG sampling module and the PPG sampling module, sampling data volumes or the sampling times of the ECG sampling module and the PPG sampling module should be the same. However, a sampling error may exist in the ECG sampling module and the PPG sampling module. Therefore, although the ECG sampling module and the PPG sampling module simultaneously start sampling, the sampling end times may be different. Therefore, the sampling end times of the ECG sampling module and the PPG sampling module are separately recorded.

To detect sampling frequency errors of the ECG sampling module and the PPG sampling module, a known reference signal needs to be found, and sampling frequencies of the ECG sampling module and the PPG sampling module on the known reference signal are separately measured, so that the sampling frequency errors of the ECG sampling module and the PPG sampling module can be learned of.

Herein, the ECG sampling module and the PPG sampling module are separately controlled to sample the standard periodic signal. The standard periodic signal is a standard signal such as a sine wave signal, a rectangular wave signal, a triangular wave signal, or a sawtooth signal, with a known and stable frequency. The standard periodic signal may be an existing periodic signal, or may be a newly generated periodic signal.

Step S103: Compensate for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold.

Specifically, after the ECG sampling module and the PPG sampling module separately sample the standard periodic signal, sampled data may be separately obtained, and after the two pieces of sampled data are separately analyzed, frequencies of the sampled data may be learned of. The obtained frequencies of the two pieces of sampled data are compared with the frequency of the standard periodic signal, so that the sampling frequency deviations of the ECG sampling module and the PPG sampling module for the standard periodic signal can be separately calculated.

Because the frequency of the standard periodic signal is stable, sampling errors for the standard periodic signal reflect system sampling errors of the ECG sampling module and the PPG sampling module. The sampling errors of the ECG sampling module and the PPG sampling module may be eliminated by compensating for the system sampling errors of the ECG sampling module and the PPG sampling module.

After the sampling frequency deviation of the ECG sampling module for the standard periodic signal is calculated, if the sampling frequency deviation of the ECG sampling module for the standard periodic signal does not exceed the preset frequency threshold, it means that the sampling frequency deviation of the ECG sampling module falls within an allowed range, and no compensation needs to be performed.

If the sampling frequency deviation of the ECG sampling module for the standard periodic signal exceeds the preset frequency threshold, the sampling frequency deviation of the ECG sampling module exceeds the allowed range, and the ECG sampling module needs to be compensated for. A purpose of compensating for the ECG sampling module is to make the sampling frequency deviation of the ECG sampling module for the standard periodic signal be less than the preset frequency threshold. A method for compensating for the ECG sampling module is increasing or decreasing a quantity of sampling points of the ECG sampling module, so as to increase or decrease the sampling frequency of the ECG sampling module.

Step S104: Compensate for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold.

Specifically, after the sampling frequency deviation of the PPG sampling module for the standard periodic signal is calculated, if the sampling frequency deviation of the PPG sampling module for the standard periodic signal does not exceed the preset frequency threshold, it means that the sampling frequency deviation of the PPG sampling module falls within the allowed range, and no compensation needs to be performed.

If the sampling frequency deviation of the PPG sampling module for the standard periodic signal exceeds the preset frequency threshold, the sampling frequency deviation of the PPG sampling module exceeds the allowed range, and the PPG sampling module needs to be compensated for. A purpose of compensating for the PPG sampling module is to make the sampling frequency deviation of the PPG sampling module for the standard periodic signal be less than the preset frequency threshold. A method for compensating for the PPG sampling module is increasing or decreasing a quantity of sampling points of the PPG sampling module, so as to increase or decrease the sampling frequency of the PPG sampling module.

A compensated sampling frequency of the ECG sampling module and a compensated sampling frequency of the PPG signal are used as new sampling frequencies of the ECG sampling module and the PPG sampling module. In this way, impact on PTT calculation due to the sampling frequency deviations of the ECG sampling module and the PPG sampling module can be eliminated.

Step S105: Compensate for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold.

After the sampling end times of the ECG sampling module and the PPG sampling module for the standard periodic signal are obtained, determining is performed on the sampling end times, so as to determine whether the sampling end time difference exceeds the preset time threshold. The preset time threshold is an allowed error range of a deviation, and may be determined based on different precision requirements for blood pressure measurement. For example, in blood pressure measurement at a home level, the preset time threshold may be set to be relatively great, but in blood pressure measurement at a medical level, the preset time threshold needs to be set to be relatively small. If the sampling end time difference between the ECG sampling module and the PPG sampling module for the standard periodic signal does not exceed the preset time threshold, it means that the sampling time deviation between the ECG sampling module and the PPG sampling module falls within an allowed range, and no compensation needs to be performed.

However, if the sampling end time difference between the ECG sampling module and the PPG sampling module for the standard periodic signal exceeds the preset time threshold, the sampling time deviation between the ECG sampling module and the PPG sampling module exceeds the allowed range, and the ECG sampling module or the PPG sampling module needs to be compensated for. The compensation may be performed on the ECG sampling module or the PPG sampling module, and may be delaying the sampling start time of the ECG sampling module or the PPG sampling module or advancing the sampling start time of the ECG sampling module or the PPG sampling module. However, generally, the sampling start time of the ECG sampling module or the PPG sampling module is delayed. In short, the sampling end time difference between the ECG sampling module and the PPG sampling module for the standard periodic signal needs to be less than the preset time threshold, and a compensated sampling start time of the ECG sampling module and a compensated sampling start time of the PPG signal are used as new sampling start times of the ECG sampling module and the PPG sampling module. In this way, impact on PTT calculation due to the time deviation between the ECG sampling module and the PPG sampling module can be eliminated.

According to the blood pressure detection signal sampling and compensation method provided in this embodiment, the ECG sampling module and the PPG sampling module are controlled to sample the standard periodic signal, so as to separately obtain the sampling frequencies and the sampling end times of the ECG sampling module and the PPG sampling module for the standard periodic signal, thereby compensating for the sampling start time of the ECG sampling module or the PPG sampling module and compensating for the sampling frequencies of the ECG sampling module and the PPG sampling module. In this way, the sampling end time difference between the ECG sampling module and the PPG sampling module for the standard periodic signal is less than the preset time threshold, and the sampling frequency deviations of the ECG sampling module and the PPG sampling module for the standard periodic signal are less than the preset frequency threshold, so that the error of the PTT determined by using the ECG sampling module and the PPG sampling module falls within the allowed range, and the error of the blood pressure value measured by using the PTT method falls within the allowed range, thereby improving precision of blood pressure measurement performed by using the PTT method.

To ensure precise synchronization between the start times of the ECG sampling module and the PPG sampling module, and the stable frequency of the sampled standard periodic signal, a high-precision clock signal is required as a basis for the time synchronization and as a basis for generating the standard periodic signal. In this case, before the standard periodic signal is sampled, the high-precision clock signal may further be generated. Precision of the high-precision clock signal is one order of magnitude higher than precision of clock signals in the ECG sampling module and the PPG sampling module. The high-precision clock signal can ensure precise recording of the sampling start times and the sampling end times of the ECG sampling module and the PPG sampling module, and ensure the stable frequency of the standard periodic signal generated based on the high-precision clock signal.

The high-precision clock signal is generated by any one of a high-precision system crystal oscillator, a synchronization calibration clock signal of a Bluetooth module, and a synchronization calibration clock signal of a Wireless Fidelity (Wireless Fidelity, WiFi) module. The high-precision clock signal includes any one of a sine wave signal, a triangular wave signal, and a sawtooth signal.

Figure 2:
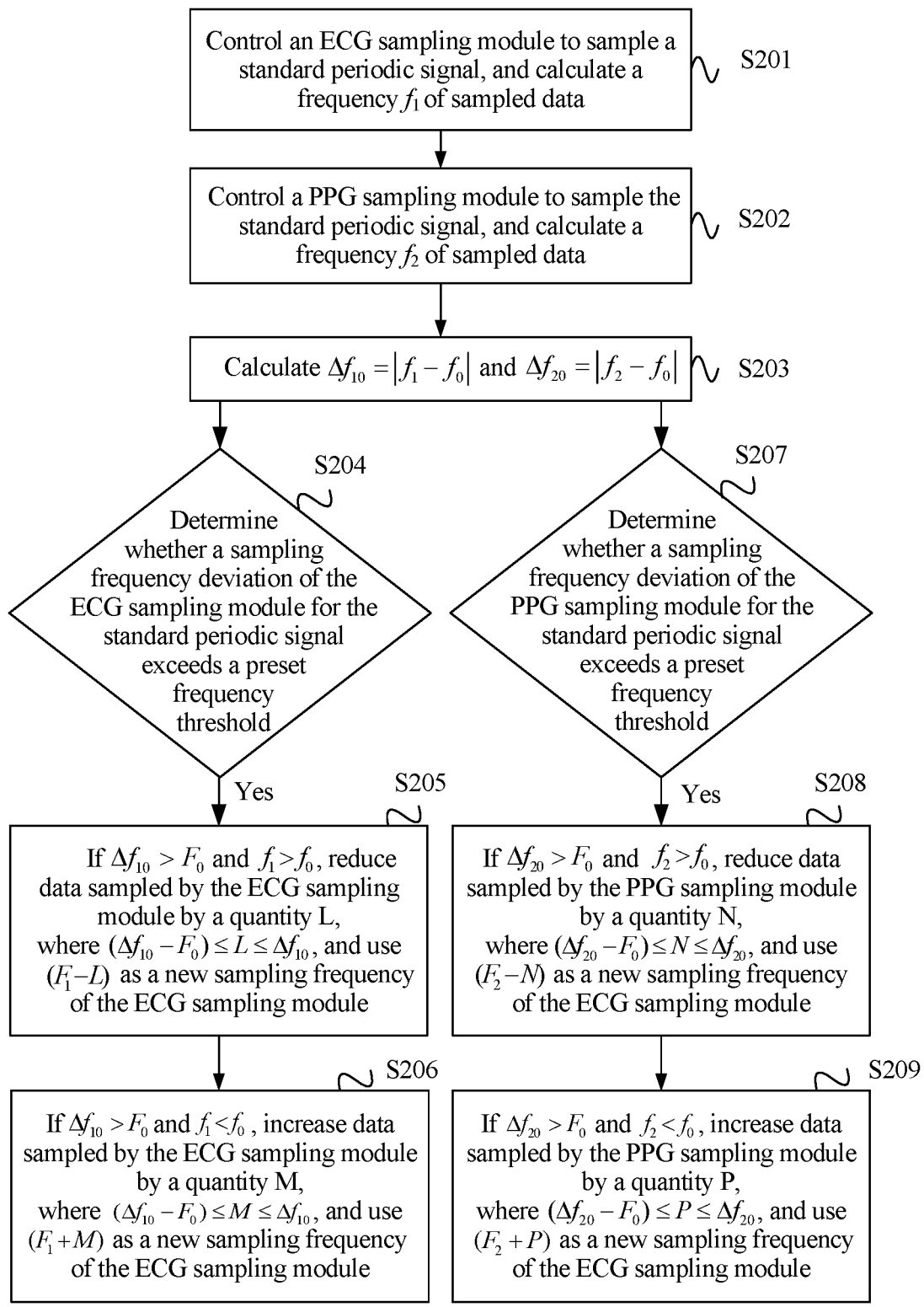
FIG. 2 is a flowchart of Embodiment 2 of a blood pressure detection signal sampling and compensation method according to an embodiment of the present invention.

FIG. 2 is a flowchart of Embodiment 2 of a blood pressure detection signal sampling and compensation method according to an embodiment of the present invention. As shown in FIG. 2, the method provided in this embodiment includes the following steps.

Step S201: Control an ECG sampling module to sample a standard periodic signal, and calculate a frequency $f_1$ of sampled data.

Step S202: Control a PPG sampling module to sample the standard periodic signal, and calculate a frequency $f_2$ of sampled data.

Specifically, the blood pressure detection signal sampling and compensation method provided in this embodiment is a specific method for compensating for a frequency error of a blood pressure detection signal. First, the ECG sampling module is controlled to sample the standard periodic signal to obtain a plurality of sampled data. Then, the frequency of the signal obtained through sampling is determined based on the obtained plurality of sampled data, and is denoted as $f_1$. The PPG sampling module is controlled to sample the standard periodic signal to obtain a plurality of sampled data. Then, the frequency of the signal obtained through sampling is determined based on the obtained plurality of sampled data, and is denoted as $f_2$. The standard periodic signal is any signal that has a fixed frequency, such as a sine wave signal, a triangular wave signal, a rectangular wave signal, or a sawtooth signal. A method for sampling the frequency of the standard periodic signal may be a maximum value method or a minimum value method. The maximum value method is extracting peak values of obtained K pieces of data to calculate frequencies $f_1^1$, $f_2^1$, . . . , and $f_K^1$ of the data, and then averaging the frequencies of the K pieces of data in K periods to obtain $f_1$, where $f_1=(f_1^1+f_2^1+ \ldots +f_K^1)/K$. Similarly, $f_2$ may be obtained according to the method, where $f_2=(f_1^2+f_2^2+ \ldots +f_K^2)/K$.

Step S203: Calculate $\Delta f_{10}=|f_1-f_0|$ and $\Delta f_{20}=|f_2-f_0|$, where $f_0$ is a frequency of the standard periodic signal, $\Delta f_{10}$ is a sampling frequency deviation of the ECG sampling module for the standard periodic signal, and $\Delta f_{20}$ is a sampling frequency deviation of the PPG sampling module for the standard periodic signal.

Specifically, after $f_1$ and $f_2$ are obtained, the sampling frequency deviations of the ECG sampling module and the PPG sampling module for the standard periodic signal may be calculated according to the formulas $\Delta f_{10}=|f_1-f_0|$ and $\Delta f_{20}=|f_2-f_0|$. $f_0$ is the frequency of the standard periodic signal. $\Delta f_{10}$ is the sampling frequency deviation of the ECG sampling module for the standard periodic signal, and $\Delta_{20}$ is the sampling frequency deviation of the PPG sampling module for the standard periodic signal.

Step S204: Determine whether the sampling frequency deviation of the ECG sampling module for the standard periodic signal exceeds a preset frequency threshold.

Specifically, whether the sampling frequency deviation of the ECG sampling module for the standard periodic signal exceeds the preset frequency threshold is determined based on a relationship between $\Delta f_{10}$ and $F_0$, where $F_0$ is the preset frequency threshold. If $\Delta f_{10} \leq F_0$, it indicates that the sampling frequency deviation of the ECG sampling module for the standard periodic signal does not exceed the preset frequency threshold. In this case, it is not necessary to compensate for a sampling frequency of the ECG sampling module. This process may be terminated. If $\Delta f_{10}>F_0$, a relationship between $f_1$ and $f_0$ further needs to be determined. If $f_1>f_0$, step S205 is performed. If $f_1<f_0$, step S206 is performed.

Step S205: If $\Delta f_{10}>F_0$ and $f_1>f_0$, reduce data sampled by the ECG sampling module by a quantity L, where $(\Delta f_{10}-F_0) \leq L \leq \Delta f_{10}$, and use $(F_1-L)$ as a new sampling frequency of the ECG sampling module, where $F_1$ is an original sampling frequency of the ECG sampling module, and $F_0$ is the preset frequency threshold.

Specifically, if $\Delta f_{10}>F_0$, it indicates that the sampling frequency deviation of the ECG sampling module for the standard periodic signal exceeds the preset frequency threshold, and $f_1>f_0$ indicates that the sampling frequency of the ECG sampling module for the standard periodic signal is greater than the frequency of the standard periodic signal. In this case, the sampling frequency of the ECG sampling module needs to be reduced. A method for reducing the sampling frequency of the ECG sampling module may be reducing the data sampled by the ECG sampling module by the quantity L, where $(\Delta f_{10}-F_0) \leq L \leq \Delta f_{10}$, so as to ensure that a sampling frequency deviation of the new sampling frequency $(F_1-L)$ of the ECG sampling module can meet a requirement. $F_1$ is the original sampling frequency of the ECG sampling module.

A method for reducing the data sampled by the ECG sampling module by the quantity L may be extracting one piece of data every a specified length l, where $l=(f_1/L)$.

Step S206: If $\Delta f_{10}>F_0$ and $f_1<f_0$, increase data sampled by the ECG sampling module by a quantity M, where $(\Delta f_{10}-F_0) \leq M \leq \Delta f_{10}$, and use $(F_1+M)$ as a new sampling frequency of the ECG sampling module.

Specifically, if $\Delta f_{10}>F_0$, it indicates that the sampling frequency deviation of the ECG sampling module for the standard periodic signal exceeds the preset frequency threshold, and $f_1<f_0$ indicates that the sampling frequency of the ECG sampling module for the standard periodic signal is less than the frequency of the standard periodic signal. In this case, the sampling frequency of the ECG sampling module needs to be increased. A method for increasing the sampling frequency of the ECG sampling module may be increasing the data sampled by the ECG sampling module by the quantity M, where $(\Delta f_{10}-F_0) \leq M \leq \Delta f_{10}$, so as to ensure that a sampling frequency deviation of the new sampling frequency $(F_1+M)$ of the ECG sampling module can meet a requirement.

A method for increasing the data sampled by the ECG sampling module by the quantity M may be adding one piece of data every a specified length m, where $m=(f_1/M)$.

Step S207: Determine whether the sampling frequency deviation of the PPG sampling module for the standard periodic signal exceeds a preset frequency threshold.

Specifically, whether the sampling frequency deviation of the PPG sampling module for the standard periodic signal exceeds the preset frequency threshold is determined based on a relationship between $\Delta f_{20}$ and $F_0$. If $\Delta f_{20} \leq F_0$, it indicates that the sampling frequency deviation of the PPG sampling module for the standard periodic signal does not exceed the preset frequency threshold. In this case, it is not necessary to compensate for a sampling frequency of the PPG sampling module. This process may be terminated. If $\Delta f_{20}>F_0$, a relationship between $f_2$ and $f_0$ further needs to be determined. If $f_2>f_0$, step S208 is performed. If $f_2<f_0$, step S209 is performed.

Step S208: If $\Delta f_{20}>F_0$ and $f_2>f_0$, reduce data sampled by the PPG sampling module by a quantity N, where $(\Delta f_{20}-F_0) \leq N \leq \Delta f_{20}$, and use $(F_2-N)$ as a new sampling frequency of the PPG sampling module, where $F_2$ is an original sampling frequency of the PPG sampling module.

Specifically, if $\Delta f_{20}>F_0$, it indicates that the sampling frequency deviation of the PPG sampling module for the standard periodic signal exceeds the preset frequency threshold, and $f_2>f_0$ indicates that the sampling frequency of the PPG sampling module for the standard periodic signal is greater than the frequency of the standard periodic signal. In this case, the sampling frequency of the PPG sampling module needs to be reduced. A method for reducing the sampling frequency of the PPG sampling module may be reducing the data sampled by the PPG sampling module by the quantity N, where $(\Delta f_{20}-F_0) \leq N \leq \Delta f_{20}$, so as to ensure that a sampling frequency deviation of the new sampling frequency $(F_2-N)$ of the PPG sampling module can meet a requirement. $F_2$ is the original sampling frequency of the PPG sampling module.

A method for reducing the data sampled by the PPG sampling module by the quantity N may be extracting one piece of data every a specified length n, where $n=(f_1/N)$.

Step S209: If $\Delta f_{20} > F_0$ and $f_2 < f_0$, increase data sampled by the PPG sampling module by a quantity P, where $(\Delta f_{20}-F_0) \leq P \leq \Delta f_{20}$, and use $(F_2+P)$ as a new sampling frequency of the PPG sampling module.

Specifically, if $\Delta f_{20} > F_0$, it indicates that the sampling frequency deviation of the PPG sampling module for the standard periodic signal exceeds the preset frequency threshold, and $f_2 < f_0$ indicates that the sampling frequency of the PPG sampling module for the standard periodic signal is less than the frequency of the standard periodic signal. In this case, the sampling frequency of the PPG sampling module needs to be increased. A method for increasing the sampling frequency of the PPG sampling module may be increasing the data sampled by the PPG sampling module by the quantity P, where $(\Delta f_{20}-F_0) \leq P \leq \Delta f_{20}$, so as to ensure that a sampling frequency deviation of the new sampling frequency $(F_2+P)$ of the PPG sampling module can meet a requirement.

A method for increasing the data sampled by the PPG sampling module by the quantity P may be adding one piece of data every a specified length p, where $p=(f_1/P)$.

Figure 3:
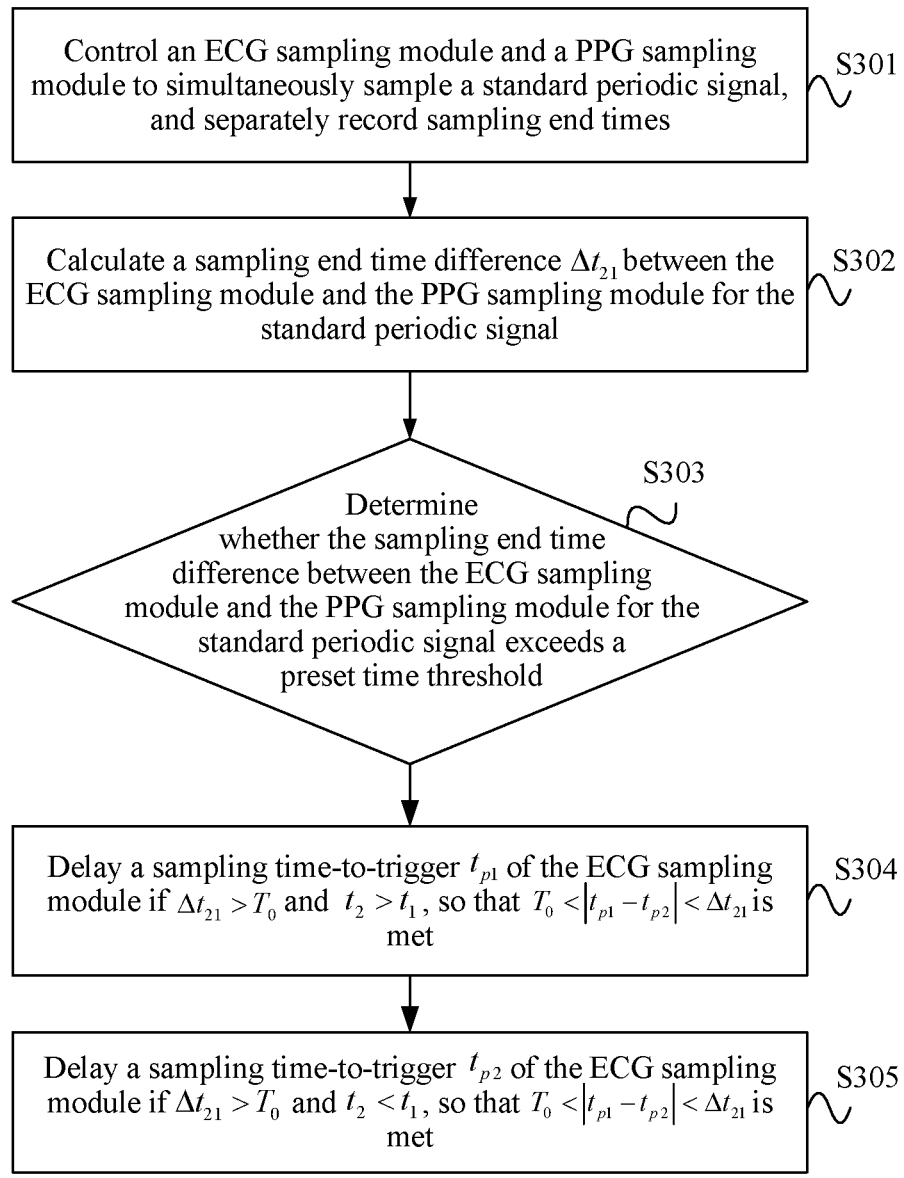
FIG. 3 is a flowchart of Embodiment 3 of a blood pressure detection signal sampling and compensation method according to an embodiment of the present invention.

FIG. 3 is a flowchart of Embodiment 3 of a blood pressure detection signal sampling and compensation method according to an embodiment of the present invention. As shown in FIG. 3, the method provided in this embodiment includes the following steps.

Step S301: Control an ECG sampling module and a PPG sampling module to simultaneously sample a standard periodic signal, and separately record sampling end times.

Specifically, a timer may be set. The timer may trigger a sampling trigger signal. When the timer expires, the ECG sampling module and the PPG sampling module are simultaneously controlled to sample the standard periodic signal. A sampling end time $t_1$ of the ECG sampling module and a sampling end time $t_2$ of the PPG sampling module are separately recorded.

Step S302: Calculate a sampling end time difference $\Delta t_{21}$ between the ECG sampling module and the PPG sampling module for the standard periodic signal, where $\Delta t_{21}=|t_2-t_1|$.

Specifically, to compensate for sampling times of the ECG sampling module and the PPG sampling module, the sampling end time difference $\Delta t_{21}$ between the ECG sampling module and the PPG sampling module for the standard periodic signal needs to be first determined, where $\Delta t_{21}=|t_2-t_1|$.

Step S303: Determine whether the sampling end time difference between the ECG sampling module and the PPG sampling module for the standard periodic signal exceeds a preset time threshold.

Specifically, whether the sampling end time difference between the ECG sampling module and the PPG sampling module for the standard periodic signal exceeds the preset time threshold is determined based on a relationship between $\Delta t_{21}$ and $T_0$, where $T_0$ is the preset time threshold. If $\Delta t_{21} \leq T_0$, it indicates that the sampling end time difference between the ECG sampling module and the PPG sampling module for the standard periodic signal does not exceed the preset time threshold. In this case, it is not necessary to compensate for the sampling times of the ECG sampling module and the PPG sampling module. This process may be terminated. If $\Delta t_{21} > T_0$, a relationship between $t_2$ and $t_1$ further needs to be determined. If $t_2 > t_1$, step S304 is performed. If $t_2 < t_1$, step S305 is performed.

Step S304: Delay a sampling time-to-trigger $t_{p1}$ of the ECG sampling module if $\Delta t_{21} > T_0$ and $t_2 > t_1$, so that $T_0 < |t_{p1}-t_{p2}| < \Delta t_{21}$ is met, where $t_{p2}$ is a sampling time-to-trigger of the PPG sampling module, and $T_0$ is the preset time threshold.

Specifically, if $\Delta t_{21} > T_0$, it indicates that the sampling end time difference between the ECG sampling module and the PPG sampling module for the standard periodic signal exceeds the preset time threshold, and $t_2 > t_1$ indicates that the sampling end time of the PPG sampling module is later than the sampling end time of the ECG sampling module. In this case, the sampling start time $t_{p1}$ of the ECG sampling module needs to be delayed, so that $T_0 < |t_{p1}-t_{p2}| < \Delta t_{21}$ is met, where $t_{p2}$ is the sampling time-to-trigger of the PPG sampling module. Certainly, the compensation for the sampling times may alternatively be implemented by advancing the sampling time-to-trigger of the PPG sampling module.

Step S305: Delay the sampling time-to-trigger $t_{p2}$ of the PPG sampling module if $\Delta t_{21} > T_0$ and $t_2 > t_1$, so that $T_0 < |t_{p1}-t_{p2}| < \Delta t_{21}$ is met.

Specifically, if $\Delta t_{21} < T_0$, it indicates that the sampling end time difference between the ECG sampling module and the PPG sampling module for the standard periodic signal exceeds the preset time threshold, and $t_2 < t_1$ indicates that the sampling end time of the PPG sampling module is earlier than the sampling end time of the ECG sampling module. In this case, the sampling start time $t_{p2}$ of the PPG sampling module needs to be delayed, so that $T_0 < |t_{p1}-t_{p2}| < \Delta t_{21}$ is met. Certainly, the compensation for the sampling times may alternatively be implemented by advancing the sampling time-to-trigger of the ECG sampling module.

Figure 4:
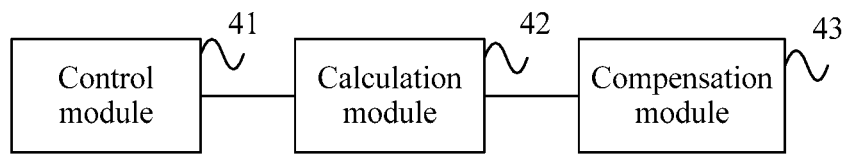
FIG. 4 is a schematic structural diagram of Embodiment 1 of a blood pressure detection signal sampling and compensation apparatus according to an embodiment of the present invention.

FIG. 4 is a schematic structural diagram of Embodiment 1 of a blood pressure detection signal sampling and compensation apparatus according to an embodiment of the present invention. As shown in FIG. 4, the blood pressure detection signal sampling and compensation apparatus provided in this embodiment includes:

a control module 41, configured to control an ECG sampling module and a PPG module to simultaneously sample a standard periodic signal;

a calculation module 42, configured to separately obtain sampling frequencies and sampling end times of the ECG sampling module and the PPG sampling module for the standard periodic signal; and a compensation module 43, configured to: compensate for a sampling frequency of the ECG sampling module if a sampling frequency deviation of the ECG sampling module for the standard periodic signal exceeds a preset frequency threshold, so that the sampling frequency deviation of the ECG sampling module for the standard periodic signal is less than the preset frequency threshold; compensate for a sampling frequency of the PPG sampling module if a sampling frequency deviation of the PPG sampling module for the standard periodic signal exceeds the preset frequency threshold, so that the sampling frequency deviation of the PPG sampling module for the standard periodic signal is less than the preset frequency threshold; and compensate for a sampling start time of the ECG sampling module or the PPG sampling module if a sampling end time difference between the ECG sampling module and the PPG sampling module for the standard periodic signal exceeds a preset time threshold, so that the sampling end time difference between the ECG sampling module and the PPG sampling module for the standard periodic signal is less than the preset time threshold.

The blood pressure detection signal sampling and compensation apparatus provided in this embodiment is configured to implement the method steps of the blood pressure detection signal sampling and compensation method shown in FIG. 1. An implementation principle and a technical effect of the apparatus are similar to those of the method. Details are not described herein.

Figure 5:
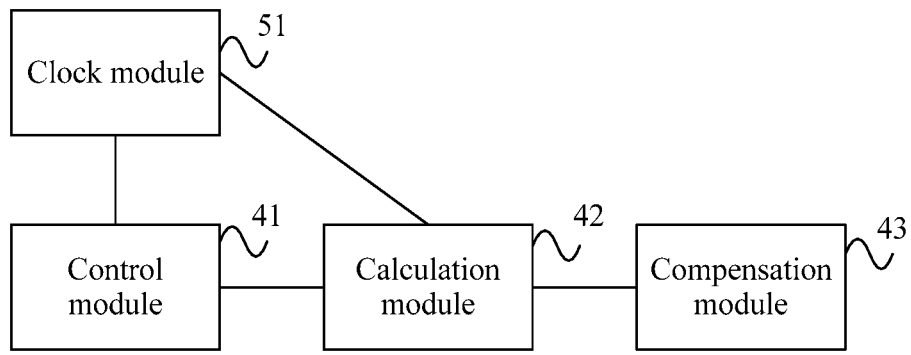
FIG. 5 is a schematic structural diagram of Embodiment 2 of a blood pressure detection signal sampling and compensation apparatus according to an embodiment of the present invention.

FIG. 5 is a schematic structural diagram of Embodiment 2 of a blood pressure detection signal sampling and compensation apparatus according to an embodiment of the present invention. As shown in FIG. 5, on a basis of FIG. 4, the blood pressure detection signal sampling and compensation apparatus provided in this embodiment further includes:

a clock module 51, configured to generate a high-precision clock signal, where precision of the high-precision clock signal is one order of magnitude higher than precision of clock signals in the ECG sampling module and the PPG sampling module.

The control module 41 is specifically configured to: control, based on the high-precision clock signal, the ECG sampling module and the PPG sampling module to simultaneously sample the standard periodic signal, and record the sampling end times of the ECG sampling module and the PPG sampling module for the standard periodic signal based on the high-precision clock signal.

Further, in the embodiment shown in FIG. 5, the high-precision clock signal is generated by any one of a high-precision system crystal oscillator, a synchronization calibration clock signal of a Bluetooth module, and a synchronization calibration clock signal of a WiFi module. The high-precision clock signal includes any one of a sine wave signal, a triangular wave signal, and a sawtooth signal.

Further, in the embodiment shown in FIG. 4 or FIG. 5, the calculation module 42 is further configured to generate the standard periodic signal based on the high-precision clock signal.

Further, in the embodiment shown in FIG. 4 or FIG. 5, the control module 41 is specifically configured to: control the ECG sampling module to sample the standard periodic signal, and calculate a frequency $f_1$ of sampled data; and control the PPG sampling module to sample the standard periodic signal, and calculate a frequency $f_2$ of sampled data. The calculation module 42 is specifically configured to calculate $\Delta f_{10}=|f_1-f_0|$ and $\Delta f_{20}=|f_2-f_0|$, where $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal. The compensation module 43 is specifically configured to: if $\Delta f_{10}>F_0$ and $f_1>f_0$, reduce data sampled by the ECG sampling module by a quantity L, where $(\Delta f_{10}-F_0) \leq L \leq \Delta f_{10}$, and use $(F_1-L)$ as a new sampling frequency of the ECG sampling module, where $F_1$ is an original sampling frequency of the ECG sampling module, and $F_0$ is the preset frequency threshold; if $\Delta f_{10}>F_0$ and $f_1<f_0$, increase data sampled by the ECG sampling module by a quantity M, where $(\Delta f_{10}-F_0) \leq M \leq \Delta f_{10}$, and use $(F_1+M)$ as a new sampling frequency of the ECG sampling module; if $\Delta f_{20}>F_0$ and $f_2>f_0$, reduce data sampled by the PPG) sampling module by a quantity N, where $(\Delta f_{20}-F_0) \leq N \leq \Delta f_{20}$, and use $(F_2-N)$ as a new sampling frequency of the PPG sampling module, where $F_2$ is an original sampling frequency of the PPG sampling module; or if $\Delta f_{20}>F_0$ and $f_2<f_0$, increase data sampled by the PPG sampling module by a quantity P, where $(\Delta f_{20}-F_0) \leq P \leq \Delta f_{20}$, and use $(F_2+P)$ as a new sampling frequency of the PPG sampling module.

Further, in the embodiment shown in FIG. 4 or FIG. 5, the calculation module 42 is further configured to calculate the sampling end time difference $\Delta t_{21}$ between the sampling module and the PPG sampling module for the standard periodic signal, where $\Delta t_{21}=|t_2-t_1|$, is a sampling end time of the ECG sampling module for the standard periodic signal, and $t_2$ is a sampling end time of the PPG sampling module for the standard periodic signal. The compensation module 43 is specifically configured to delay a sampling time-to-trigger $t_{p1}$ of the ECG sampling module if $\Delta t_{21}>T_0$ and $t_2>t_1$, so that $T_0<|t_{p1}-t_{p2}|<\Delta t_{21}$ is met, where $t_{p2}$ is a sampling time-to-trigger of the PPG sampling module, and $T_0$ is the preset time threshold; or delay a sampling time-to-trigger $t_{p2}$ of the PPG sampling module if $\Delta t_{21}>T_0$ and $t_2<t_1$, so that $T_0<|t_{p1}-t_{p2}|<\Delta t_{21}$ is met.

Figure 6:
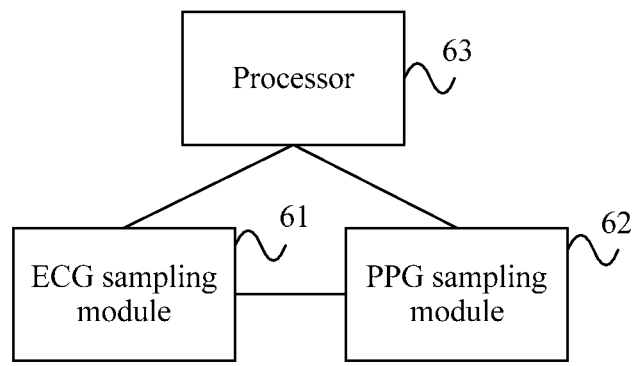
FIG. 6 is a schematic structural diagram of Embodiment 1 of a blood pressure signal sampling system according to an embodiment of the present invention.

FIG. 6 is a schematic structural diagram of Embodiment 1 of a blood pressure signal sampling system according to an embodiment of the present invention. As shown in FIG. 6, the blood pressure signal sampling system provided in this embodiment includes an ECG sampling module 61, a PPG sampling module 62, and a processor 63.

The processor 63 is configured to: control the ECG sampling module 61 and the PPG module 62 to simultaneously sample a standard periodic signal; separately obtain sampling frequencies and sampling end times of the ECG sampling module 61 and the PPG sampling module 62 for the standard periodic signal; compensate for a sampling frequency of the ECG sampling module 61 if a sampling frequency deviation of the ECG sampling module 61 for the standard periodic signal exceeds a preset frequency threshold, so that the sampling frequency deviation of the ECG sampling module 61 for the standard periodic signal is less than the preset frequency threshold; compensate for a sampling frequency of the PPG sampling module 62 if a sampling frequency deviation of the PPG sampling module 62 for the standard periodic signal exceeds the preset frequency threshold, so that the sampling frequency deviation of the PPG sampling module 62 for the standard periodic signal is less than the preset frequency threshold; and compensate for a sampling start time of the ECG sampling module 61 or the PPG sampling module 62 if a sampling end time difference between the ECG sampling module 61 and the PPG sampling module 62 for the standard periodic signal exceeds a preset time threshold, so that the sampling end time difference between the ECG sampling module 61 and the PPG sampling module 62 for the standard periodic signal is less than the preset time threshold.

Specifically, the blood pressure signal sampling system provided in this embodiment may be any system that can perform blood pressure detection according to a PTT method, for example, a home wrist blood pressure monitor and arm blood pressure monitor, or any medical blood pressure monitor. The blood pressure signal sampling system includes the ECG sampling module 61 and the PPG sampling module 62. The ECG sampling module 61 is configured to collect an electrocardiogram signal of a user, is constituted by an electrocardiogram sensor and an electrocardiogram signal sampling chip, and may use an integrated analog front end chip (for example, ADS1292) or a discrete sampling chip. The PPG sampling module 62 is constituted by a PPG optical sensor and a PPG sampling chip, and may use an integrated analog front end chip (for example, AFE4404/ADPD153) or a discrete sampling chip.

The processor 63 may be any hardware chip having a processing function.

Figure 7:
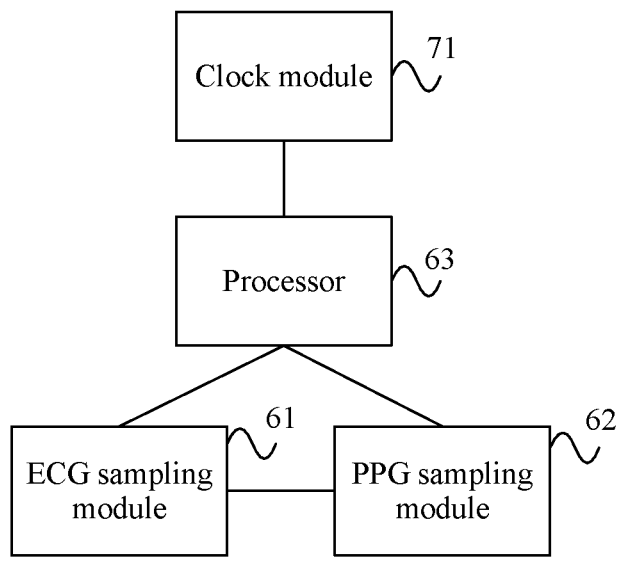
FIG. 7 is a schematic structural diagram of Embodiment 2 of a blood pressure signal sampling system according to an embodiment of the present invention.

FIG. 7 is a schematic structural diagram of Embodiment 2 of a blood pressure signal sampling system according to an embodiment of the present invention. As shown in FIG. 7, on a basis of FIG. 6, the blood pressure signal sampling system provided in this embodiment further includes:

a clock module 71, configured to generate a high-precision clock signal, where precision of the high-precision clock signal is one order of magnitude higher than precision of clock signals in the ECG sampling module 61 and the PPG sampling module 62.

The processor 63 is specifically configured to: control, based on the high-precision clock signal, the ECG sampling module 61 and the PPG sampling module 62 to simultaneously sample the standard periodic signal, and record the sampling end times of the ECG sampling module 61 and the PPG sampling module 62 for the standard periodic signal based on the high-precision clock signal.

The clock module 71 may be any one of a high-precision system crystal oscillator, a clock module in a Bluetooth module, and a clock module in a Wireless Fidelity WiFi module. The high-precision clock signal includes any one of a sine wave signal, a triangular wave signal, and a sawtooth signal.

Further, in the embodiment shown in FIG. 6 or FIG. 7, the processor 63 is further configured to generate the standard periodic signal based on the high-precision clock signal.

Further, in the embodiment shown in FIG. 6 or FIG. 7, the processor 63 is specifically configured to: control the ECG sampling module 61 to sample the standard periodic signal, and calculate a frequency $f_1$ of sampled data; control the PPG sampling module 62 to sample the standard periodic signal, and calculate a frequency $f_2$ of sampled data; calculate $\Delta f_{10}=|f_1-f_0|$ and $\Delta f_{20}=|f_2-f_0|$, where $f_0$ is a frequency of the standard periodic signal, $\Delta f_{10}$ is the sampling frequency deviation of the ECG sampling module 61 for the standard periodic signal, and $\Delta f_{20}$ is the sampling frequency deviation of the PPG sampling module 62 for the standard periodic signal; and if $\Delta f_{10}>F_0$ and $f_1>f_0$, reduce data sampled by the ECG sampling module 61 by a quantity L, where $(\Delta f_{10}-F_0) \leq L \leq \Delta f_{10}$, and use $(F_1-L)$ as a new sampling frequency of the ECG sampling module 61, where $F_1$ is an original sampling frequency of the ECG sampling module 61, and $F_0$ is the preset frequency threshold; if $\Delta f_{10}>f_0$ and $f_1<f_0$, increase data sampled by the ECG sampling module 61 by a quantity M, where $(\Delta f_{10}-F_0) \leq M \leq \Delta f_{10}$, and use $(F_1+M)$ as a new sampling frequency of the ECG sampling module 61; if $\Delta f_{20}>F_0$ and $f_2>f_0$, reduce data sampled by the PPG sampling module 62 by a quantity N, where $(\Delta f_{20}-F_0) \leq N \leq \Delta f_{20}$, and use $(F_2-N)$ as a new sampling frequency of the PPG sampling module 62, where $F_2$ is an original sampling frequency of the PPG sampling module 62; or if $\Delta f_{20}>F_0$ and $f_2<f_0$, increase data sampled by the PPG sampling module 62 by a quantity P, where $(\Delta f_{20}-F_0) \leq P \leq \Delta f_{20}$, and use $(F_2+P)$ as a new sampling frequency of the PPG sampling module 62.

Further, in the embodiment shown in FIG. 6 or FIG. 7, the processor 63 is specifically configured to: calculate the sampling end time difference $\Delta t_{21}$ between the ECG sampling module 61 and the PPG sampling module 62 for the standard periodic signal, where $\Delta t_{21}=|t_2-t_1|$, $t_1$ is a sampling end time of the ECG sampling module 61 for the standard periodic signal, and $t_2$ is a sampling end time of the PPG sampling module 62 for the standard periodic signal; and delay a sampling time-to-trigger $t_{p1}$ of the ECG sampling module 61 if $\Delta t_{21}\,T_0$ and $t_2>t_1$, so that $T_0<|t_{p1}-t_{p2}|<\Delta t_{21}$ is met, where $t_{p2}$ is a sampling time-to-trigger of the PPG sampling module 62, and $T_0$ is the preset time threshold; or delay a sampling time-to-trigger $t_{p2}$ of the PPG sampling module 62 if $\Delta t_{21}>T_0$ and $t_2<t_1$, so that $T_0<|t_{p1}-t_{p2}|<\Delta t_{21}$ is met.

Persons of ordinary skill in the art may understand that all or some of the steps of the method embodiments may be implemented by a program instructing relevant hardware. The program may be stored in a computer-readable storage medium. When the program runs, the steps of the method embodiments are performed. The foregoing storage medium includes: any medium that can store program code, such as a ROM, a RAM, a magnetic disk, or an optical disc.

Finally, it should be noted that the foregoing embodiments are merely intended for describing the technical solutions of the present invention, but not for limiting the present invention. Although the present invention is described in detail with reference to the foregoing embodiments, persons of ordinary skill in the art should understand that they may still make modifications to the technical solutions described in the foregoing embodiments or make equivalent replacements to some or all technical features thereof. Therefore, the protection scope of the present invention shall be subject to the protection scope of the claims.

What is claimed is:

1. A blood pressure detection signal sampling and compensation method, comprising:
controlling an electrocardiogram (ECG) sampling module and a photoplethysmogram (PPG) sampling module to simultaneously sample a standard periodic signal;
separately obtaining sampling frequencies and sampling end times of the ECG sampling module and the PPG sampling module for the standard periodic signal;
compensating for a sampling frequency of the ECG sampling module if a sampling frequency deviation of the ECG sampling module for the standard periodic signal exceeds a preset frequency threshold, wherein the compensating causes the sampling frequency deviation of the ECG sampling module for the standard periodic signal is less than the preset frequency threshold;
compensating for a sampling frequency of the PPG sampling module if a sampling frequency deviation of the PPG sampling module for the standard periodic signal exceeds the preset frequency threshold, wherein the compensating causes the sampling frequency deviation of the PPG sampling module for the standard periodic signal is less than the preset frequency threshold; and
compensating for a sampling start time of the ECG sampling module or the PPG sampling module if a sampling end time difference between the ECG sampling module and the PPG sampling module for the standard periodic signal exceeds a preset time threshold, wherein the compensating causes the sampling end time difference between the ECG sampling module and the PPG sampling module for the standard periodic signal is less than the preset time threshold.

2. The method according to claim 1, wherein before the controlling an ECG sampling module and a PPG sampling module to simultaneously sample a standard periodic signal, the method further comprises:
generating a high-precision clock signal, wherein precision of the high-precision clock signal is one order of magnitude higher than precision of clock signals in the ECG sampling module and the PPG sampling module;

the controlling an ECG sampling module and a PPG sampling module to simultaneously sample a standard periodic signal comprises:
  controlling, based on the high-precision clock signal, the ECG sampling module and the PPG sampling module to simultaneously sample the standard periodic signal; and
the separately obtaining sampling frequencies and sampling end times of the ECG sampling module and the PPG sampling module for the standard periodic signal comprises:
  recording the sampling end times of the ECG sampling module and the PPG sampling module for the standard periodic signal based on the high-precision clock signal.

3. The method according to claim 2, wherein the high-precision clock signal is generated by any one of a high-precision system crystal oscillator, a synchronization calibration clock signal of a Bluetooth module, and a synchronization calibration clock signal of a Wireless Fidelity (WiFi) module; and
the high-precision clock signal comprises:
  any one of a sine wave signal, a triangular wave signal, and a sawtooth signal.

4. The method according to claim 2, wherein before the controlling an ECG sampling module and a PPG sampling module to separately sample a standard periodic signal, the method further comprises:
  generating the standard periodic signal based on the high-precision clock signal.

5. The method according to claim 3, wherein before the controlling an ECG sampling module and a PPG sampling module to separately sample a standard periodic signal, the method further comprises:
  generating the standard periodic signal based on the high-precision clock signal.

6. The method according to claim 5, wherein the controlling an ECG sampling module and a PPG sampling module to separately sample a standard periodic signal comprises:
  controlling the ECG sampling module to sample the standard periodic signal, and calculating a frequency $f_1$ of sampled data; and
  controlling the PPG sampling module to sample the standard periodic signal, and calculating a frequency $f_2$ of sampled data;
the separately obtaining sampling frequencies and sampling end times of the ECG sampling module and the PPG sampling module for the standard periodic signal comprises:
  calculating $\Delta f_{10}=|f_1-f_0|$ and $\Delta f_{20}=|f_1-f_0|$ wherein $f_0$ is a frequency of the standard periodic signal, $\Delta f_{10}$ is the sampling frequency deviation of the ECG sampling module for the standard periodic signal, and $\Delta f^{20}$ is the sampling frequency deviation of the PPG sampling module for the standard periodic signal;
the compensating for a sampling frequency of the ECG sampling module if a sampling frequency deviation of the ECG sampling module for the standard periodic signal exceeds a preset frequency threshold, wherein the compensating causes the sampling frequency deviation of the ECG sampling module for the standard periodic signal is less than the preset frequency threshold comprises:
  if $\Delta f_{10}>F_0$ and $f_1>f_0$, reducing data sampled by the ECG sampling module by a quantity L, wherein $(\Delta f_{10}-F_0) \leq L \leq \Delta f_{10}$, and using $(F_1-L)$ a new sampling frequency of the ECG sampling module, wherein $F_1$ is an original sampling frequency of the ECG sampling module, and $F_0$ is the preset frequency threshold; or
  if $\Delta f_{10}>F_0$ and $f_1<f_0$, increasing data sampled by the ECG sampling module by a quantity M, wherein $(\Delta f_{10}-F_0) \leq M \leq \Delta f_{10}$ and using $(F_1+M)$ as a new sampling frequency of the ECG sampling module; and
the compensating for a sampling frequency of the PPG sampling module if a sampling frequency deviation of the PPG sampling module for the standard periodic signal exceeds the preset frequency threshold, wherein the compensating causes the sampling frequency deviation of the PPG sampling module for the standard periodic signal is less than the preset frequency threshold comprises:
  if $\Delta f_{20}>F_0$ and $f_2>f_0$, reducing data sampled by the PPG sampling module by a quantity N, wherein and using $(\Delta f_{20}-F_0) \leq N \leq \Delta f_{20}$ as a new sampling frequency of the PPG sampling module, wherein $F_2$ is an original sampling frequency of the PPG sampling module; or
  if $\Delta f_{20}>F_0$ and $f_2<f_0$, increasing data sampled by the PPG sampling module by a quantity P, wherein $(\Delta f_{20}-F_0) \leq P \leq \Delta f_{20}$, and using $(F_2+P)$ as a new sampling frequency of the PPG sampling module.

7. The method according to claim 6, wherein the compensating for a sampling start time of the ECG sampling module or the PPG sampling module if a sampling end time difference between the ECG sampling module and the PPG sampling module for the standard periodic signal exceeds a preset time threshold, wherein the sampling end time difference between the ECG sampling module and the PPG sampling module for the standard periodic signal is less than the preset time threshold comprises:
  calculating the sampling end time difference $\Delta t_{21}$ between the ECG sampling module and the PPG sampling module for the standard periodic signal, wherein $\Delta t_{21}=|t_2-t_1|$, $t_1$ is a sampling end time of the ECG sampling module for the standard periodic signal, and $t_2$ sampling end time of the PPG sampling module for the standard periodic signal; and
  delaying a sampling time-to-trigger $t_{p1}$ of the ECG sampling module if $\Delta t_{21}>T_0$ and $t_2>t_1$, wherein the delaying causes $T_0<|t_{p1}-t_{p2}|<\Delta t_{21}$ to be met, wherein $t_{p2}$ is a sampling time-to-trigger of the PPG sampling module, and $T_0$ is the preset time threshold; or
  delaying a sampling time-to-trigger $t_{p2}$ of the PPG sampling module if $\Delta t_{21}>T_0$ and $t_2<t_1$, wherein delaying causes $T_0<|t_{p1}-t_{p2}|<\Delta t_{21}$ to be met.

8. The method according to claim 1, wherein the controlling an ECG sampling module and a PPG sampling module to separately sample a standard periodic signal comprises:
  controlling the ECG sampling module to sample the standard periodic signal, and calculating a frequency $f_1$ of sampled data; and
  controlling the PPG sampling module to sample the standard periodic signal, and calculating a frequency $f_2$ of sampled data;
the separately obtaining sampling frequencies and sampling end times of the ECG sampling module and the PPG sampling module for the standard periodic signal comprises:
  calculating $\Delta f_{10}=|f_1-f_0|$, wherein $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal;

the compensating for a sampling frequency of the ECG sampling module if a sampling frequency deviation of the ECG sampling module for the standard periodic signal exceeds a preset frequency threshold, wherein the compensating causes the sampling frequency deviation of the ECG sampling module for the standard periodic signal is less than the preset frequency threshold comprises:

if $\Delta f_{10} > f_0$ and $f_1 > f_0$, reducing data sampled by the ECG sampling module by a quantity L, wherein $(\Delta f_{10} - f_0) \leq L \leq \Delta f_{10}$, and using $(f_1 - L)$ as a new sampling frequency of the ECG sampling module, wherein $f_1$ is an original sampling frequency of the ECG sampling module, and $f_0$ is the preset frequency threshold; or if $\Delta f_{10} > f_0$ and $f_1 < f_0$, increasing data sampled by the ECG sampling module by a quantity M, wherein $(\Delta f_{10} - f_0) \leq M \leq \Delta f_{10}$, and using $(f_1 + M)$ as a new sampling frequency of the ECG sampling module; and the compensating for a sampling frequency of the PPG sampling module if a sampling frequency deviation of the PPG sampling module for the standard periodic signal exceeds the preset frequency threshold, wherein the compensating causes the sampling frequency deviation of the PPG sampling module for the standard periodic signal is less than the preset frequency threshold comprises:

if $\Delta f_{20} > F_0$ and $f_2 > f_0$, reducing data sampled by the PPG sampling module by a quantity N, wherein $(\Delta f_{20} - F_0) \leq N \leq \Delta f_{20}$, and using $(F_2 - N)$ as a new sampling frequency of the PPG sampling module, wherein $F_2$ is an original sampling frequency of the PPG sampling module; or if $\Delta f_{20} > F_0$ and $f_2 < f_0$, increasing data sampled by the PPG sampling module by a quantity P, wherein $(\Delta f_{20} - F_0) \leq P \leq \Delta f_{20}$, and using $(F_2 + P)$ as a new sampling frequency of the PPG sampling module.

9. The method according to claim 1, wherein the compensating for a sampling start time of the ECG sampling module or the PPG sampling module if a sampling end time difference between the ECG sampling module and the PPG sampling module for the standard periodic signal exceeds a preset time threshold, wherein the compensating causes the sampling end time difference between the ECG sampling module and the PPG sampling module for the standard periodic signal is less than the preset time threshold comprises:

calculating the sampling end time difference $\Delta t_{21}$ between the ECG sampling module and the PPG sampling module for the standard periodic signal, wherein $\Delta t_{21} = |t_2 - t_1|$, $t_1$ is a sampling end time of the ECG sampling module for the standard periodic signal, and $t_2$ is a sampling end time of the PPG sampling module for the standard periodic signal; and delaying a sampling time-to-trigger $t_{p1}$ of the ECG sampling module if $\Delta t_{21} > T_0$ and $t_2 > t_1$ wherein the delaying causes $T_0 < |t_{p1} - t_{p2}| < \Delta t_{21}$ to be met, wherein $t_{p2}$ is a sampling time-to-trigger of the PPG sampling module, and $T_0$ is the preset time threshold; or delaying a sampling time-to-trigger $t_{p2}$ of the PPG sampling module if $\Delta t_{21} > T_0$ and $t_2 < t_1$, wherein the delaying causes $T_0 < |t_{p1} - t_{p2}| < \Delta t_{21}$ to be met.

10. A blood pressure signal sampling system, comprising an electrocardiogram (ECG) sampling module, a photoplethysmogram (PPG) sampling module, and at least one processor, wherein the processor is configured to:

control the ECG sampling module and the PPG module to simultaneously sample a standard periodic signal;

separately obtain sampling frequencies and sampling end times of the ECG sampling module and the PPG sampling module for the standard periodic signal;

compensate for a sampling frequency of the ECG sampling module if a sampling frequency deviation of the ECG sampling module for the standard periodic signal exceeds a preset frequency threshold, wherein the compensating causes the sampling frequency deviation of the ECG sampling module for the standard periodic signal to be less than the preset frequency threshold;

compensate for a sampling frequency of the PPG sampling module if a sampling frequency deviation of the PPG sampling module for the standard periodic signal exceeds the preset frequency threshold, wherein the compensating causes the sampling frequency deviation of the PPG sampling module for the standard periodic signal to be less than the preset frequency threshold; and compensate for a sampling start time of the ECG sampling module or the PPG sampling module if a sampling end time difference between the ECG sampling module and the PPG sampling module for the standard periodic signal exceeds a preset time threshold, wherein the compensating causes the sampling end time difference between the ECG sampling module and the PPG sampling module for the standard periodic signal to be less than the preset time threshold.

11. The system according to claim 10, further comprising a clock module, the clock module configured to generate a high-precision clock signal, wherein precision of the high-precision clock signal is one order of magnitude higher than precision of clock signals in the ECG sampling module and the PPG sampling module; and the at least one processor is configured to:

control, based on the high-precision clock signal, the ECG sampling module and the PPG sampling module to simultaneously sample the standard periodic signal; and record the sampling end times of the ECG sampling module and the PPG sampling module for the standard periodic signal based on the high-precision clock signal.

12. The system according to claim 11, wherein the clock module comprises any one of a high-precision system crystal oscillator, a clock module in a Bluetooth module, and a clock module in a Wireless Fidelity (WiFi) module;

the high-precision clock signal is generated by any one of the high-precision system crystal oscillator, a synchronization calibration clock signal of the Bluetooth module, and a synchronization calibration clock signal of the WiFi module; and the high-precision clock signal comprises:

any one of a sine wave signal, a triangular wave signal, and a sawtooth signal.

13. The system according to claim 11, wherein the at least one processor is further configured to generate the standard periodic signal based on the high-precision clock signal.

14. The system according to claim 12, wherein the at least one processor is further configured to generate the standard periodic signal based on the high-precision clock signal.

15. The system according to claim 14, wherein the at least one processor is configured to:

control the ECG sampling module to sample the standard periodic signal, and calculate a frequency $f_1$ of sampled data;

control the PPG sampling module to sample the standard periodic signal, and calculate a frequency $f_2$ of sampled data; calculate $\Delta f_{10}=|f_1-f_0|$ and $\Delta f_{20}=|f_2-f_0|$, wherein $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal; and if $\Delta f_{10}>F_0$ and $f_1>f_0$, reduce data sampled by the ECG sampling module by a quantity L, wherein $(\Delta f_{10}-F_0)\leq L\leq \Delta f_{10}$, and use $(F_1-L)$ as a new sampling frequency of the ECG sampling module, wherein $F_1$ is an original sampling frequency of the ECG sampling module, and $F_0$ is the preset frequency threshold; if $\Delta f_{10}>F_0$ and $f_1<f_0$, increase data sampled by the ECG sampling module by a quantity M, wherein $(\Delta f_{10}-F_0)\leq M\leq \Delta f_{10}$, and use $(F_1+M)$ as a new sampling frequency of the ECG sampling module; if $\Delta f_{20}>F_0$ and $f_2>f_0$ reduce data sampled by the PPG sampling module by a quantity N, wherein $(\Delta f_{20}-F_0)\leq N\leq \Delta f_{20}$, and use $(F_2-N)$ as a new sampling frequency of the PPG sampling module, wherein $F_2$ is an original sampling frequency of the PPG sampling module; or if $\Delta f_{20}>F_0$ and $f_2<f_0$, increase data, sampled by the PPG sampling module by a quantity P, wherein $(\Delta f_{20}-F_0)\leq P\leq \Delta f_{20}$ $(F_2+P)$ as a new sampling frequency of the PPG sampling module.

16. The system according to claim 15, wherein the at least one processor is configured to:

calculate the sampling end time difference $\Delta t_{21}$ between the ECG sampling module and the PPG sampling module for the standard periodic signal, wherein $\Delta t_{21}=|t_2-t_1|$, $t_1$ is a sampling end time of the ECG sampling module for the standard periodic signal, and $t_2$ is a sampling end time of the PPG sampling module for the standard periodic signal; and delay a sampling time-to-trigger $t_{p1}$ of the ECG sampling module if $\Delta t_{21}>T_0$ and $t_2>t_1$, wherein the delaying causes $T_0<|t_{p1}-t_{p2}|<\Delta t_{21}$ to be met, wherein $t_{p2}$ is a sampling time-to-trigger of the PPG sampling module, and $T_0$ is the preset time threshold; or delay a sampling time-to-trigger $t_{p2}$ of the PPG sampling module if $\Delta t_{21}>T_0$ and $t_2<t_1$, wherein the delaying causes $T_0<|t_{p1}-t_{p2}|<\Delta t_{21}$ to be met.

17. The system according to claim 10, wherein the at least one processor is configured to:

control the ECG sampling module to sample the standard periodic signal, and calculate a frequency $f_1$ of sampled data;

control the PPG sampling module to sample the standard periodic signal, and calculate a frequency $f_2$ of sampled data;

calculate $\Delta f_{10}=|f_1-f_0|$ and $\Delta f_{20}=|f_2-f_0|$, wherein $f_0$ is a frequency of the standard periodic signal, $\Delta f_{10}$ is the sampling frequency deviation of the ECG sampling module for the standard periodic signal, and $\Delta f_{20}$ is the sampling frequency deviation of the PPG sampling module for the standard periodic signal; and if $\Delta f_{10}>F_0$ and $f_1>f_0$, reduce data sampled by the ECG sampling module by a quantity L, wherein $(\Delta f_{10}-F_0)\leq L\leq \Delta f_{10}$, and use $(F_1-L)$ as a new sampling frequency of the ECG sampling module, wherein $F_1$ is an original sampling frequency of the ECG sampling module, and $F_0$ is the preset frequency threshold;

if $\Delta f_{10}>F_0$ and $f_1<f_0$, increase data sampled by the ECG sampling module by a quantity M, wherein $(\Delta f_{10}-F_0)\leq M\leq \Delta f_{10}$, and use $(F_1+M)$ as a new sampling frequency of the ECG sampling module;

if $\Delta f_{20}>F_0$ and $f_2>f_0$, reduce data sampled by the PPG sampling module by a quantity N, wherein $(\Delta f_{20}-F_0)\leq N\leq \Delta f_{20}$ and use $(F_2-N)$ as a new sampling frequency of the PPG sampling module, wherein $F_2$ is an original sampling frequency of the PPG sampling module; or if $\Delta f_{20}>F_0$ and $f_2<f_0$, increase data sampled by the PPG sampling module by a quantity P, wherein $(\Delta f_{20}-F_0)\leq P\leq \Delta f_{20}$, and use $(F_2+P)$ as a new sampling frequency of the PPG sampling module.

18. The system according to claim 10, wherein the at least one processor is configured to:

calculate the sampling end time difference $\Delta t_{21}$ between the ECG sampling module and the PPG sampling module for the standard periodic signal, wherein $\Delta t_{21}=|t_2-t_1|$, is a sampling end time of the ECG sampling module for the standard periodic signal, and $t_2$ is a sampling end time of the PPG sampling module for the standard periodic signal; and delay a sampling time-to-trigger $t_{p1}$ of the ECG sampling module if $\Delta t_{21}>T_0$ and $t_2>t_1$, wherein the delaying causes $T_0<|t_{p1}-t_{p2}|<\Delta t_{21}$ to be met, wherein $t_{p2}$ is a sampling time-to-trigger of the PPG sampling module, and $T_0$ is the preset time threshold; or delay a sampling time-to-trigger $t_{p2}$ of the PPG sampling module if $\Delta t_{21}>T_0$ and $t_2<t_1$, wherein the delaying causes $T_0<|t_{p1}-t_{p2}|<\Delta t_{21}$ to be met.

* * * * *

UNITED STATES PATENT AND TRADEMARK OFFICE
CERTIFICATE OF CORRECTION

PATENT NO. : 11,375,908 B2
APPLICATION NO. : 16/072265
DATED : July 5, 2022
INVENTOR(S) : Yongtao Jiang, Yu Zhu and Peida Xu It is certified that error appears in the above-identified patent and that said Letters Patent is hereby corrected as shown below:

In the Claims

Column 21 / Line 50 - In Claim 6, delete second occurrence of "$|f_1-f_0|$" and insert -- $|f_2-f_0|$, --.

Column 21 / Line 54 - In Claim 6, delete "$\Delta f^{20}$" and insert -- $\Delta f_{20}$ --.

Column 22 / Line 6 - In Claim 6, delete "$\Delta f_{10}$" and insert -- $\Delta f_{10}$, --.

Column 22 / Line 17 - In Claim 6, after "wherein" insert -- $(\Delta f_{20}-F_0) \leq N \leq \Delta f_{20}$, --.

Column 22 / Line 18 - In Claim 6, delete "$(\Delta f_{20}-F_0) \leq N \leq \Delta f_{20}$" and insert -- $(F_2-N)$ --.

Column 22 / Line 62 - In Claim 8, delete "$\Delta f_{10}=|f_1-f_0|$, wherein" and insert -- $\Delta f_{10}=|f_1-f_0|$ and $\Delta f_{20}=|f_2-f_0|$, wherein --.

Column 23 / Line 9 (Approx.) - In Claim 8, delete "$\Delta f_{10}>f_0$" and insert -- $\Delta f_{10}>F_0$ --.

Column 23 / Line 10 (Approx.) - In Claim 8, delete "$f_0$)" and insert -- $F_0$) --.

Column 23 / Line 11 (Approx.) - In Claim 8, delete "($f_1$" and insert -- ($F_1$ --.

Column 23 / Line 12 (Approx.) - In Claim 8, delete "$f_1$" and insert -- $F_1$ --.

Column 23 / Line 15 (Approx.) - In Claim 8, delete "$f_0$" and insert -- $F_0$ --.

Column 23 / Line 16 (Approx.) - In Claim 8, delete "$\Delta f_{10}>f_0$" and insert -- $\Delta f_{10}>F_0$ --.

Column 23 / Line 18 (Approx.) - In Claim 8, delete "($\Delta f_{10}>f_0$)" and insert -- ($\Delta f_{10}>F_0$) --.

Column 23 / Line 18 (Approx.) In Claim 8, delete "($f_1$" and insert -- ($F_1$ --.

Signed and Sealed this
Eighteenth Day of April, 2023

Katherine Kelly Vidal
*Director of the United States Patent and Trademark Office*

Column 25 / Line 22 - In Claim 15, delete "$f_2>f_0$" and insert -- $f_2>f_0$, --.

Column 25 / Line 29 (Approx.) - In Claim 15, delete "$\Delta f_{20}$" and insert -- $\Delta f_{20}$, and use --.

Column 26 / Line 36 (Approx.) - In Claim 18, after "," insert -- $t_1$ --.